United States Patent
Senderos et al.

(10) Patent No.: US 10,234,432 B2
(45) Date of Patent: Mar. 19, 2019

(54) DEVICE AND METHOD TO DETECT CRACKS IN THE COUNTERSINK OF A FASTENER

(71) Applicant: The Boeing Company, Chicago, IL (US)

(72) Inventors: Bruno Zamorano Senderos, Huntsville, AL (US); Daniel E. Sievers, Owens Cross Roads, AL (US)

(73) Assignee: the boeing company, Chicago, IL (US)

( * ) Notice: Subject to any disclaimer, the term of this patent is extended or adjusted under 35 U.S.C. 154(b) by 120 days.

(21) Appl. No.: 15/228,940

(22) Filed: Aug. 4, 2016

(65) Prior Publication Data
US 2018/0038836 A1    Feb. 8, 2018

(51) Int. Cl.
| | | |
|---|---|---|
| *G01N 29/22* | (2006.01) | |
| *G01N 29/48* | (2006.01) | |
| *G01N 29/50* | (2006.01) | |

(52) U.S. Cl.
CPC .......... *G01N 29/48* (2013.01); *G01N 29/223* (2013.01); *G01N 29/50* (2013.01); *G01N 2291/0231* (2013.01); *G01N 2291/0289* (2013.01); *G01N 2291/0427* (2013.01); *G01N 2291/106* (2013.01); *G01N 2291/2694* (2013.01)

(58) Field of Classification Search
CPC .. G01N 29/48; G01N 29/043; G01N 29/0091; G01N 29/46; G01N 29/246; G01N 29/262; G01N 29/245; G01N 29/2475; G01N 29/223; G01N 29/50; G01M 5/0033; G01M 5/0066; G01M 5/0091
See application file for complete search history.

(56) References Cited

U.S. PATENT DOCUMENTS

| | | | |
|---|---|---|---|
| 4,366,711 A * | 1/1983 | Weilbacher | G01N 29/041 376/252 |
| 5,767,410 A | 6/1998 | Lareau et al. | |
| 6,996,480 B2 | 2/2006 | Giurgiutiu et al. | |
| 8,176,786 B2 | 5/2012 | Sohn et al. | |
| 8,208,344 B2 * | 6/2012 | Paget | G01S 5/22 367/127 |
| 8,532,940 B2 * | 9/2013 | Yan | G01N 29/07 702/35 |
| 8,585,283 B1 * | 11/2013 | Doyle | G01N 29/2475 374/43 |
| 9,127,998 B1 * | 9/2015 | Guldiken | G01L 5/246 |
| 9,194,769 B1 * | 11/2015 | Senibi | G06F 11/00 |
| 9,239,315 B1 * | 1/2016 | Georgeson | G01N 29/04 |
| 2003/0009300 A1 * | 1/2003 | Giurgiutiu | G01N 29/11 702/35 |
| 2004/0221652 A1 * | 11/2004 | Flora | G01N 29/041 73/578 |

(Continued)

Primary Examiner — Helen C Kwok
(74) Attorney, Agent, or Firm — MH2 Technology Law Group LLP (57) ABSTRACT

Disclosed are methods and systems to nondestructively detect cracks at or near a countersink of a fastener, such as a rivet, in a thin walled structure using Lamb waves. Generation and detection of Lamb waves at symmetric locations relative to the fastener provides signals used to calculate a symmetry parameter. The symmetry parameter represents a comparison of the relative amplitudes of the detected Lamb wave signals and provides a simple indication of whether a crack exists.

21 Claims, 8 Drawing Sheets

(56) References Cited

U.S. PATENT DOCUMENTS

| | | | |
|---|---|---|---|
| 2005/0209791 A1* | 9/2005 | Senibi | G01N 29/041 702/33 |
| 2005/0228597 A1* | 10/2005 | Giurgiutiu | G01M 5/0033 702/35 |
| 2006/0062696 A1* | 3/2006 | Chow | B01L 3/502746 422/400 |
| 2006/0287842 A1* | 12/2006 | Kim | G01H 9/004 702/183 |
| 2007/0012111 A1* | 1/2007 | Kim | G01H 9/004 73/594 |
| 2007/0012112 A1* | 1/2007 | Kim | G01H 9/004 73/594 |
| 2007/0240512 A1* | 10/2007 | Takada | G01N 29/041 73/588 |
| 2007/0261493 A1* | 11/2007 | Kim | G01M 5/0033 73/594 |
| 2007/0282541 A1* | 12/2007 | Griess | H04Q 9/00 702/34 |
| 2008/0225376 A1* | 9/2008 | Kim | G01H 9/004 359/287 |
| 2009/0157358 A1* | 6/2009 | Kim | G01L 1/16 702/185 |
| 2009/0301198 A1* | 12/2009 | Sohn | G01N 29/069 73/598 |
| 2010/0162825 A1* | 7/2010 | Karp | G01M 5/0033 73/799 |
| 2010/0312493 A1* | 12/2010 | Purekar | G01N 17/02 702/35 |
| 2011/0023610 A1* | 2/2011 | Ume | G01N 29/11 73/622 |
| 2013/0327148 A1* | 12/2013 | Yan | G01N 29/34 73/628 |
| 2015/0338306 A1* | 11/2015 | Dunne | G01M 5/0033 73/587 |
| 2016/0274062 A1* | 9/2016 | Takahashi | B23P 6/00 |
| 2017/0234837 A1* | 8/2017 | Hall | G01N 29/2431 73/602 |
| 2018/0031525 A1* | 2/2018 | Philtron | G01N 29/043 |
| 2018/0045688 A1* | 2/2018 | Ziehl | G01N 29/4409 |

* cited by examiner

DEVICE AND METHOD TO DETECT CRACKS IN THE COUNTERSINK OF A FASTENER

FIELD

The present teachings relate generally to systems and methods for non-destructive evaluation and, more particularly, to systems and methods for non-destructively detecting cracks near a fastener of a thin-walled structure.

BACKGROUND

Many industries use thin walled structures joined by fasteners. For example, thin-walled metal panels joined by rivets form the skin of an aircraft and other vehicles. Routine operation of the aircraft subjects the skin to harsh environments that includes large temperature changes and high stress. As a result, cracks in the skin can form. Cracks at or near the rivets can also form during manufacturing of the aircraft. Nondestructive methods for detecting cracks in these structures include radiography, eddy current, and ultrasonic methods. These methods, however, suffer from several problems.

Cracks in a countersink of a rivet, for example, cause particular problems in the aircraft industry. Radiography can be used to detect these cracks, but the technique is limited to detection of large cracks. Eddy currents can detect cracks that extend at least 100 mil past the rivet head, however, for detection of smaller cracks, particularly in the countersink, the fasteners need to be removed first. Eddy current methods are also limited to conductive materials. Ultrasonic methods, using a phased array, can detect smaller sized cracks in the countersink without first removing the fastener. However, this technique requires surface preparation and a contact media. Ultrasonic methods are also time consuming and expensive. Laser generated interferometry techniques also exist, but the low intensity waves that are generated are difficult to measure in an industrial environment. Another drawback is that each of the above methods requires a highly trained operator to conduct the testing and analyze the results.

An improved method and system for detecting cracks at and near a fastener is desired.

SUMMARY

The following presents a simplified summary in order to provide a basic understanding of some aspects of one or more examples of the present teachings. This summary is not an extensive overview, nor is it intended to identify key or critical elements of the present teachings, nor to delineate the scope of the disclosure. Rather, its primary purpose is merely to present one or more concepts in simplified form as a prelude to the detailed description presented later.

In an aspect, a method for detecting cracks in a structure is provided. A first Lamb wave can be generated at a first location, wherein the first Lamb wave propagates towards a fastener in the structure. At a first detector position, a first signal corresponding to the first Lamb wave can be detected subsequent to its interaction with the fastener. A second Lamb wave can be generated at the first location. At a second detector position, a second signal corresponding to the second Lamb wave can be detected subsequent to its interaction with the fastener, wherein the second detector position is symmetric to the first detector position relative to the fastener and the first location. A first symmetry parameter can then be calculated from the first signal and the second signal, wherein the first symmetry parameter comprises a value representing a comparison of an amplitude of the first signal and an amplitude of the second signal.

In another aspect, a further method for detecting cracks in a structure is provided. A first Lamb wave can be generated at a first location, wherein the first Lamb wave propagates towards a fastener in the structure. At a first detector position, a first signal corresponding to the first Lamb wave can be detected subsequent to its interaction with the fastener. A second Lamb wave can be generated at a second location, wherein the second location is symmetrical to the first location relative to the fastener and the first detector position. At the first detector position, a second signal corresponding to the second Lamb wave can be detected subsequent to its interaction with the fastener. A first symmetry parameter can then be calculated from the first signal and the second signal, wherein the first symmetry parameter comprises a value representing a comparison of an amplitude of the first signal and an amplitude of the second signal.

A system for detecting cracks in a structure is also provide. The system includes a Lamb wave generation device that generates a first Lamb wave that propagates towards a fastener in the structure and that generates a second Lamb wave that propagates towards the fastener. The system further includes a Lamb wave detection device that provides a first signal corresponding to the first Lamb wave subsequent to its interaction with the fastener and provides a second signal corresponding to the second Lamb wave subsequent to its interaction with the fastener. The system also includes a positioning system that positions the Lamb wave detection device to measure the first signal at a first position and to measure the second signal at second position, wherein the first position is symmetrical to the second position relative to the fastener and the Lamb wave generation device. The system further includes a computing system having one or more processors and a memory system comprising one or more non-transitory computer readable media storing instructions that, when executed by the one or more processors, causes the computing system to calculate a symmetry parameter from the first signal and second signal and compare the symmetry parameter to a predetermined threshold, wherein the symmetry parameter comprises a value representing a comparison of an amplitude of the first signal and an amplitude of the second signal.

In another aspect, a method for detecting cracks in a structure is provided. In the method, a first Lamb wave can be generated at a first location, wherein the first Lamb wave propagates towards a fastener in the structure. At a first detector position, a first signal corresponding to the first Lamb wave subsequent to its interaction with the fastener can be detected. At a second detector position, a second signal corresponding to the first Lamb wave subsequent to its interaction with the fastener, can also be detected, wherein the second detector position is symmetric to the first detector position relative to the fastener and the first location. A first symmetry parameter can then be calculated from the first signal and the second signal, wherein the first symmetry parameter comprises a value representing a comparison of an amplitude of the first signal and an amplitude of the second signal.

BRIEF DESCRIPTION OF THE DRAWINGS

The accompanying drawings, which are incorporated in and constitute a part of this specification, illustrate examples of the present teachings and together with the description, serve to explain the principles of the disclosure. In the figures.

It should be noted that some details of the figures have been simplified and are drawn to facilitate understanding of the present teachings rather than to maintain strict structural accuracy, detail, and scale.

DETAILED DESCRIPTION

Reference will now be made in detail to exemplary examples of the present teachings, examples of which are illustrated in the accompanying drawings. Wherever possible, the same reference numbers will be used throughout the drawings to refer to the same or like parts.

Systems and methods of the present teachings utilize Lamb waves to detect the presence of a crack at and near the countersink of a fastener in thin-walled structures. Ultrasonic Lamb waves are not commonly used for nondestructive evaluation because they are difficult to generate with conventional transducers and only propagate between two surfaces, for example, opposite surfaces of a plate or sheet. Propagation of these waves requires the plate or sheet have a thickness comparable with the Lamb wave wavelength. This feature, however, makes them ideal for testing of thin walled structures, such as, for example, aircraft skin. The exemplary systems and methods disclosed herein avoid the need to remove the fasteners for the detection of cracks within the countersink. Furthermore, use of a symmetry parameter, based on the detection of two Lamb waves at opposite sides of a fastener, can provide a simple indication of the presence of a crack without the need to use highly skilled technicians to operate the equipment and analyze the results.

As used herein, a "symmetry parameter" is a numerical value that represents a comparison of the relative amplitudes of two or more detected Lamb wave signals, where the position of detection of the two or more Lamb waves is symmetrical to the location of generation of the two or more Lamb waves. Prior to calculating the symmetry parameter, the detected Lamb wave signals can be subject to signal processing.

Figure 1A:
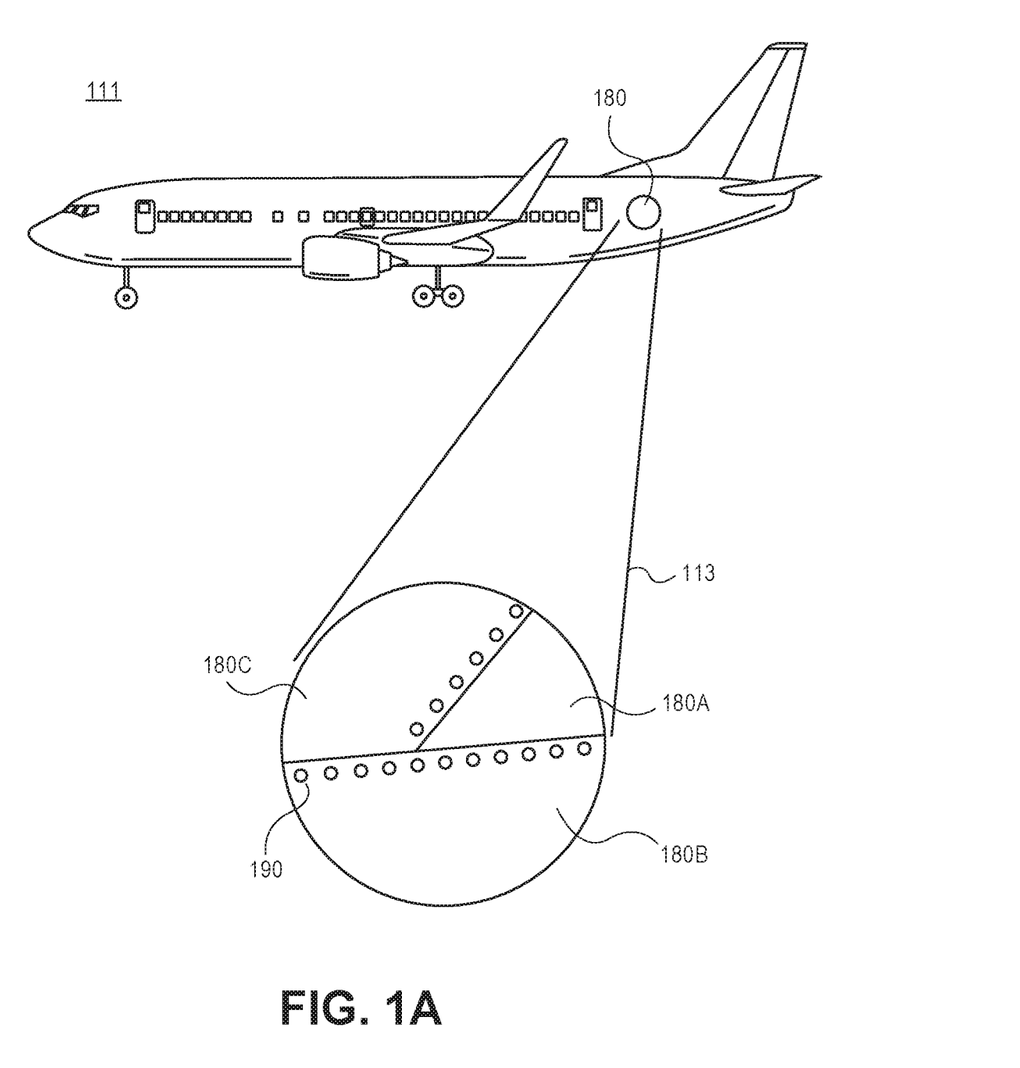
FIG. 1A depicts an aircraft having an aircraft skin fastened with countersunk rivets.

FIG. 1A depicts an aircraft 111. A portion of aircraft skin 180 is shown in an enlarged view 113. Aircraft skin 180 can be formed of several thin walled structures or panels, depicted as panels 180a, 180b, and 180c, that are fastened by countersunk rivets such as countersunk rivet 190. Although the exemplary methods and systems described herein relate to inspecting an aircraft skin with rivets, it should be understood that the disclosed methods and systems are not limited to inspecting aircraft skin fastened with rivets and can be used on other thin-walled structures with other types of fasteners.

Figure 1B:
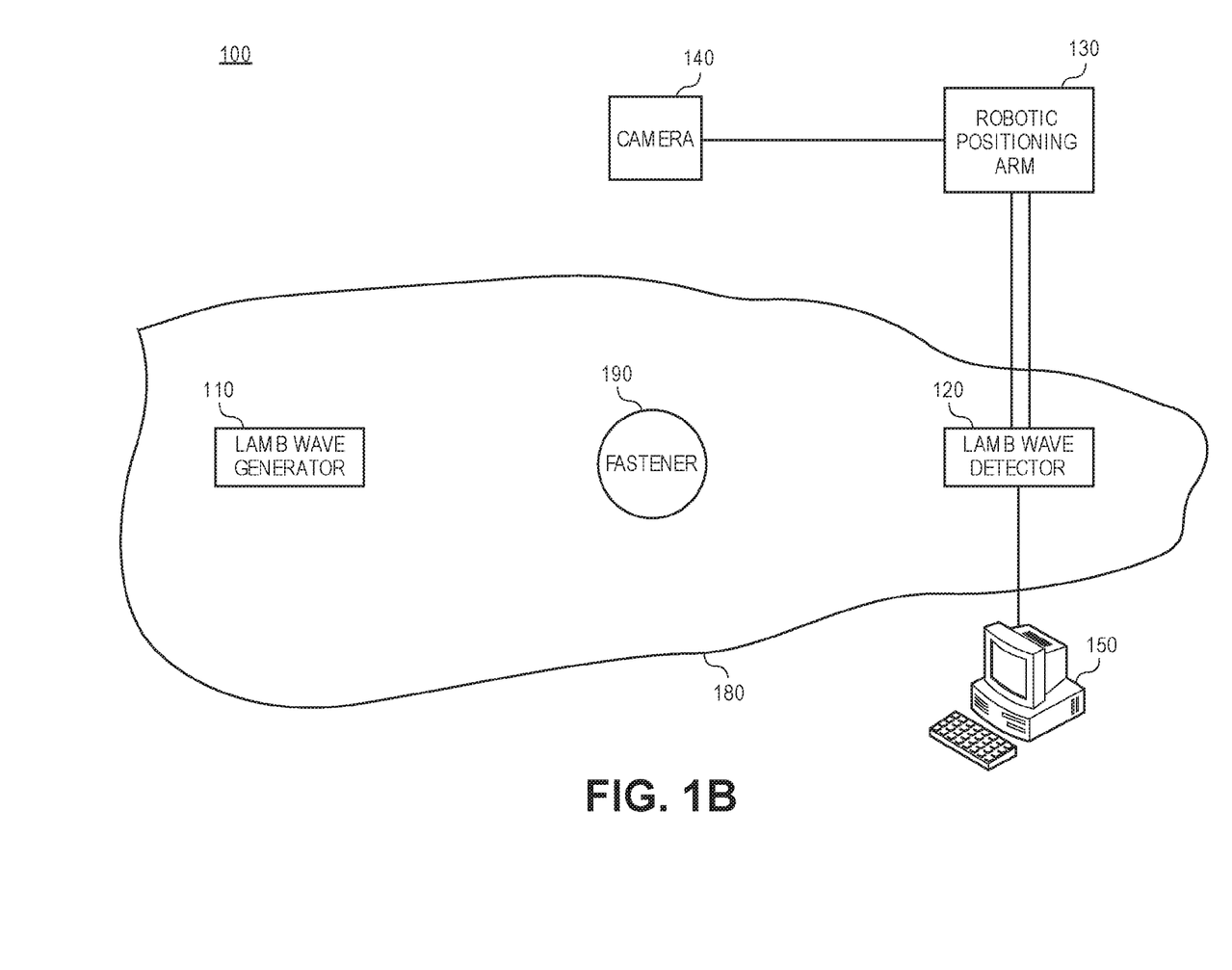
FIGS. 1B and 1C depict systems for detecting cracks in thin walled structures using Lamb waves in accordance with examples of the present teachings.

FIG. 1B depicts an exemplary non-destructive system 100 for detecting cracks at the countersink of a fastener in a thin walled structure. System 100 includes a Lamb wave generator 110 that can be moved to various locations near a fastener, depicted as a rivet 190 in aircraft skin 180. Exemplary non-destructive system 100 further includes a Lamb wave detector 120 that can be mounted on a robotic positioning arm 130. Robotic positioning arm 130 working in conjunction with a camera 140 can move Lamb wave detector to various positions near rivet 190. Robotic positioning arm 130 and camera 140 can be part of an automated system that positions the Lamb wave generator and/or detector. Non-destructive system 100 also includes a computer device 150.

Lamb wave generator 110 can be, for example, an electro-magnetic acoustic transducer ("EMAT"), a superconducting electro-magnetic acoustic transducer ("SEMAT"), a pulsed laser, or capacitance coupling device. It can also be an impacting device, a piezoelectric transducer, such as a lead zirconate titanate (PZT) transducer, or other ultrasonic wave generating devices that contacts a surface of the thin walled structure.

Lamb wave detector 120 can be a laser interferometer or any other contact or non-contact device for detection of Lamb waves. Examples of other Lamb wave detectors include, but are not limited to capacitive sensors, air coupled acoustic transducers, EMAT, SEMAT, eddy current sensors, or vibrometers. In an example, Lamb wave detector 120 can include at least two detectors spaced apart from each other. Lamb wave detector 120 can include signal conditioning capabilities.

Robotic positioning arm 130 can be, for example, at least a 5 axis positioning system that includes 2 axes for positioning in a plane of the thin walled structure being inspected, 1 axis for the distance related to the plane, and 2 additional axes to position parallel to the measurement plane and rotation to perform the measurement. Alternatively robot positioning arm 130 can be at least a two axis positioning system for XY positioning in the plane of the Lamb wave propagation and a rolling system that maintains parallelism and distance with the surface of the thin walled structure being examined. Robot positioning arm can be, for example, an Adept Viper robot from Omron Adept Technologies, Inc. (San Ramon, Calif.).

Camera 140 can be a digital camera or a video camera. Cameras that use polarized light or dark field images can also be used. Camera 140 should provide sufficient contrast to differentiate the rivet or other fastener from the thin walled structure.

Computer device 150 can be, for example, a laptop computer, desktop computer, tablet computer, mobile phone, and the like. The computer device 1500 can be any type of computer device that includes one or more processors of varying core configurations and clock frequencies. The computer device 150 can also include one or more memory devices that serve as a main memory during the operation of the computer device 150. The computer device 150 can also include one or more peripheral interfaces, such as keyboards, mice, touchpads, displays (monitors), touchscreens, etc., for enabling human interaction with and manipulation of the computer device 150. For example, computer device 150 can include an indicator such as a light or display to show the detection of a crack. The computer device 150 can also include one or more storage devices of varying physical dimensions and storage capacities, such as flash drives, hard drives, random access memory, etc., for storing data, such as images, files, and program instructions for execution by the one or more processors. Computer device 150 can include signal conditioning capabilities.

Figure 1C:
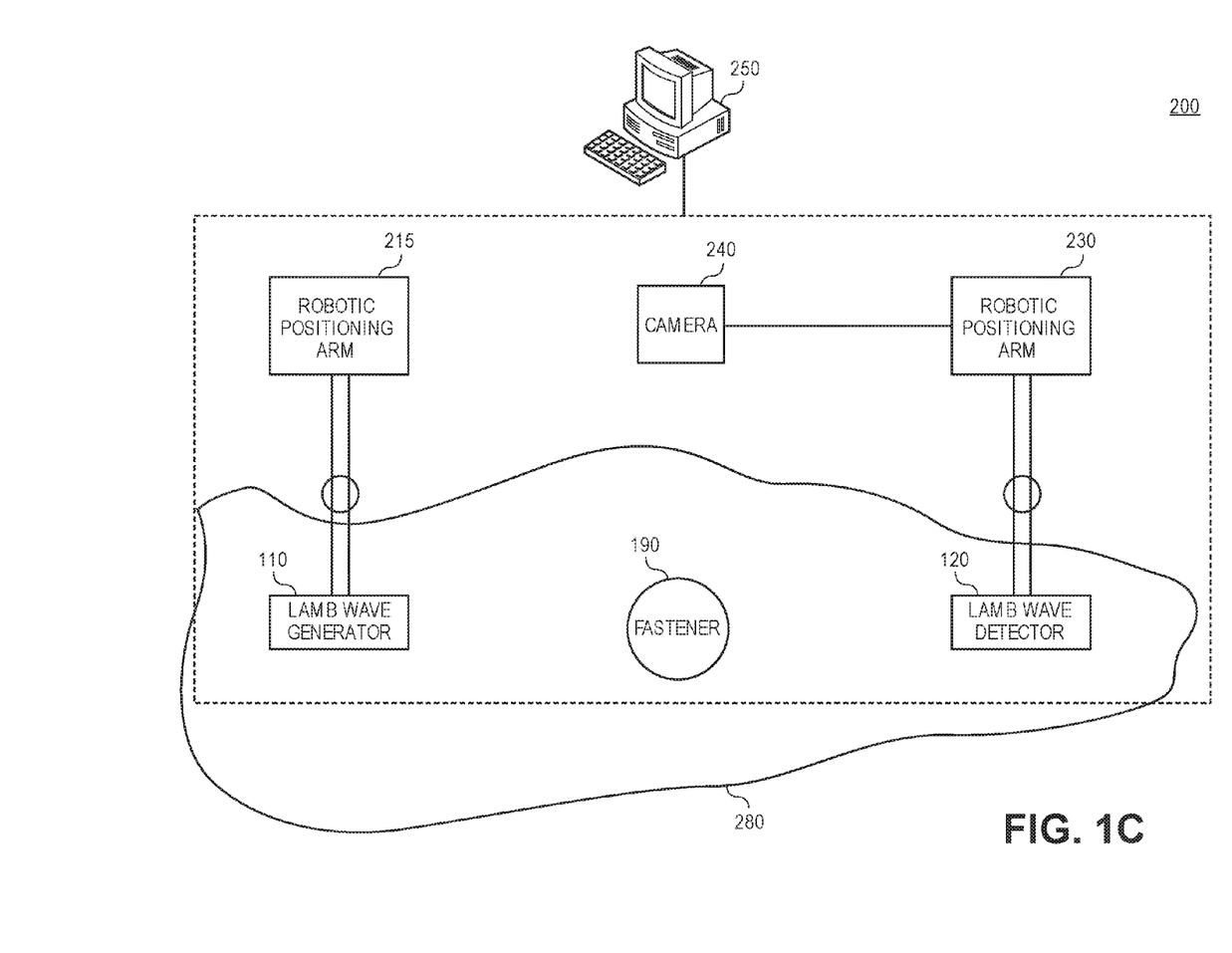

FIG. 1C depicts another exemplary non-destructive system for detecting cracks at or near the countersink of a fastener in a thin walled structure. Non-destructive system 200 shown in FIG. 1C is similar to system 100 shown in FIG. 1B, except in system 200 both the Lamb wave detector and generator can be positioned by one or more robotic positioning arms. System 200 includes a Lamb wave generator 210 that can be moved to various locations near a fastener, depicted as a rivet 290 in thin walled structure 280. Lamb wave generator 210 can be mounted on a first robotic positioning arm 215. First robotic positioning arm 215 can work in conjunction with camera 240 to move Lamb wave generator 210 to the desired location. Exemplary non-destructive system 200 further includes a Lamb wave detector 220 that can be mounted on a second robotic positioning arm 230. Second robotic positioning arm 230 working in conjunction either with camera 240 or another camera (not shown) can move Lamb wave detector 220 to various positions near rivet 190. Non-destructive system 200 also includes a computer device 250. One of ordinary skill in the art will understand that other components may be included as part of the exemplary systems.

Figure 2:
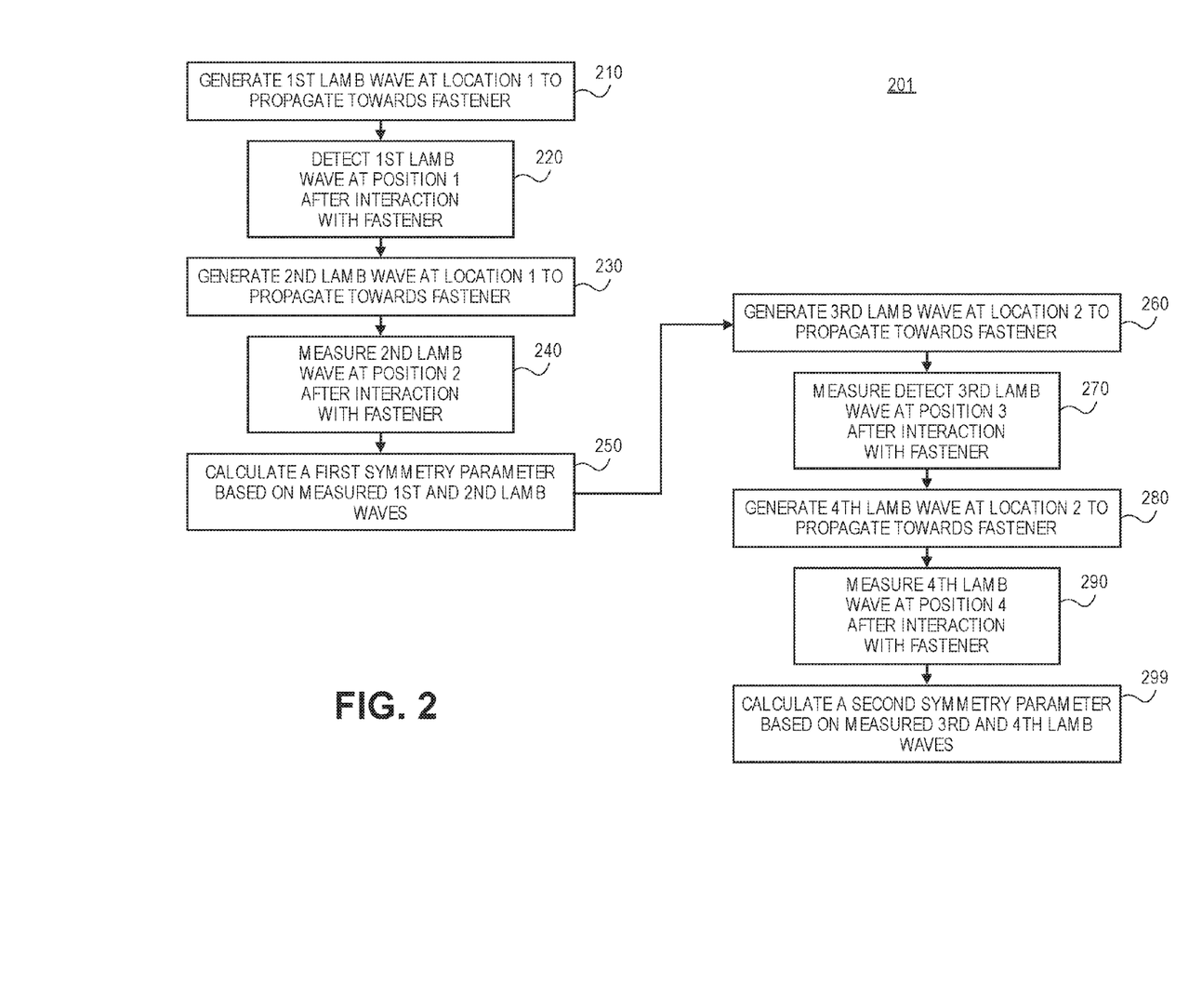
FIG. 2 depicts a method for detecting cracks in thin walled structures using Lamb waves in accordance with an example of the present teachings.

FIG. 2 depicts an exemplary method 201 for nondestructively detecting cracks at the countersink of a fastener. In exemplary method 201, Lamb waves are detected at two symmetrical detection positions for each Lamb wave generation location. At 210, a first Lamb wave is generated at a first location. For example, referring to FIG. 1B, SEMAT 110 can generate a first Lamb wave in aircraft skin 180 that propagates towards rivet 190. Although the exemplary method and FIGS refer to a rivet in a metal aircraft skin, one of ordinary skill in the art will understand that the method can be performed on other thin walled structures formed of metals or composites to detect cracks at and near other types of fasteners.

At 220, subsequent to the first Lamb wave interacting with the countersunk rivet 190, the first Lamb wave is detected at a first position. For example, referring to FIG. 1B, Lamb wave detector 120 can detect the first Lamb wave in aircraft skin 180 after it interacts with the countersunk rivet 190.

At 230, a second Lamb wave is generated at the first location on the aircraft skin. The second Lamb wave also propagates towards the rivet.

At 240, subsequent to its interaction with the rivet and/or countersink, the second Lamb wave is detected at a second position. The second position (where the second Lamb wave is detected) is symmetrical to the first position (where the first Lamb wave is detected) with respect to the rivet and the first location (where both the first and second lamb waves are generated). Referring back to FIG. 1B, camera 140 and robotic positioning arm 130 can move Lamb wave detector 120 to the first position and the second position.

Figure 3A:
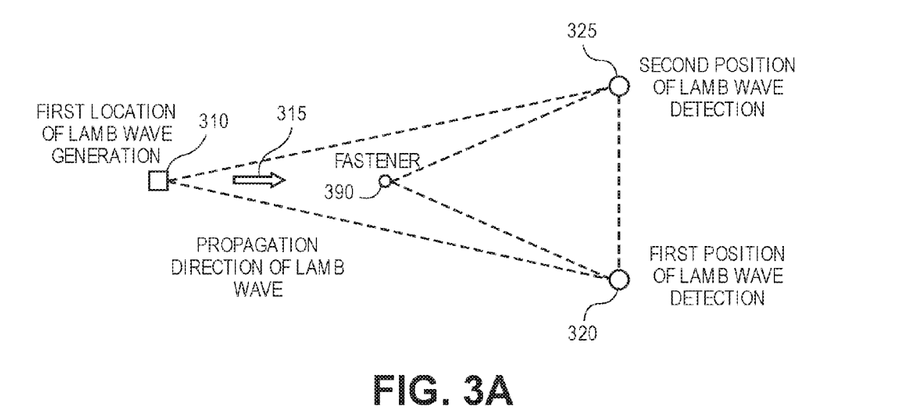
FIGS. 3A and 3B depict a symmetry of the detected Lamb waves in accordance with examples of the present teachings.

The symmetry is further illustrated in FIG. 3A, where a first Lamb wave is generated at a first location 310. The first Lamb wave propagates in a direction represented by arrow 315 towards a rivet 390. One of ordinary skill in the art will understand that rivet 390 represents the location of, for example, a countersink where cracks can occur. After the first Lamb wave interacts with rivet and/or countersink 390, it is detected at a first position 320. A second Lamb wave is then generated at first location 310 to propagate in the direction represented by arrow 315 towards rivet 390. After the second Lamb wave interacts with rivet and/or countersink 390, it is detected at a second position 325. As shown by the dotted lines, first position 320 is symmetrical to second position 325 with respect to rivet 390 and first location 310. In other words, first location 310, first position 320, and second position 325 form an isosceles triangle. Similarly, location of rivet 390, first position 320, and second position 325 also form an isosceles triangle. Although the Lamb wave generator, detector, and rivet are depicted on a planar surface, one of ordinary skill in the art will understand that the method and systems disclosed herein can be used to detect cracks on curved surfaces.

At 250, of exemplary method 201, a first symmetry parameter is calculated based on the first and second Lamb waves detected at the first and second positions. Referring back to FIGS. 1A and 1B, computer device 150, 250 can calculate the symmetry parameter, compare it to a threshold in order to determine whether a crack exists, and provide an indication to an operator. The symmetry parameter represents a comparison of the detected Lamb waves, for example, their amplitudes, and represents that comparison as a value. The threshold can be set depending on a number of factors, for example, a predetermined threshold can be set based on a previous symmetry parameter calculated from earlier measurement of Lamb wave interaction with the fastener. The predetermined threshold can also be set based on symmetry parameters calculated from previous measurements of similar fasteners on similar thin walled structures. The predetermined threshold can also be set based on symmetry parameters determined by modeling Lamb wave propagation. The threshold can also depend on how the detected Lamb wave signals are processed after detection. In one example, the symmetry parameter can be set above and below 1, where 1 indicates perfect symmetry. For example, the threshold parameter can be a ratio of the amplitudes of the detected Lamb waves and the threshold can be set at less than or equal to 0.8 and greater than or equal to 1.2. An indication that a crack has been detected will be provided if the symmetry parameter exceeds the threshold. The threshold can also be a range with an upper value and a lower value. Exceeding either the upper value or exceeding the lower value can indicate the presence of a crack.

The symmetry parameter can be calculated from the detected Lamb waves in number of ways. Examples include, but are not limited to, performing cross correlation, integration, direct subtraction with integration, signal envelope, wavelet, and discrete wavelet operations on the detected Lamb wave signals. In a cross correlation method, a temporal cross correlation of a detected Lamb wave signal and its symmetric detected Lamb wave signal can be calculated. For example, referring to FIG. 3A, the temporal cross correlation of the Lamb waves detected at first position 320 and second position 325 can be calculated. The symmetry parameter is the inverse of the maximum of the cross correlation and will be 1 for perfect symmetry. A value of less 1 indicates lack of symmetry of the amplitudes of the detected Lamb waves. The symmetry parameter can then be compared to the set threshold to determine whether a crack has been detected.

The symmetry parameter can also be calculated using an integration method. In this method, a time of arrival of the two Lamb waves at the Lamb wave detector can be defined. Again referring to FIG. 3A, once the time of arrival has been defined for the first Lamb wave detected at first position 320 and the second Lamb wave at second position 325, the detected signals can be integrated for the defined time starting at the time of arrival. If the detected signals are similar, the integral will have the same value. The symmetry can be defined by subtracting the integrals and taking the absolute value. In this case, the symmetry parameter starts at 0 indicating perfect symmetry (indicating no crack), and grows larger in value as the lack of symmetry increases. While several methods have been provided, one of ordinary skill in the art will understand that other methods can be used to compare the amplitude of the Lamb wave signals and calculate the symmetry parameter.

Prior to calculating the symmetry parameter, signal processing can be performed on the detected Lamb wave signals. For example, the detected Lamb wave signals can be filtered, subject to a Hilbert transformation, and an analytic function calculated to define the signal envelope. Once determined, the signal envelope can be used in the methods described above to calculate the symmetry parameter.

Wavelet methods can also be used to process the signals before calculation of the symmetry parameter. From the processed signals, a pseudo-frequency can be selected and subject to the cross-correlation, integration, or direct subtraction methods described above to calculate the symmetry parameter. For example, continuous wavelet analysis can be used to analyze how the frequency content of a signal changes over time. While examples of signal processing have been provided, it should be understood that other signal processing methods are contemplated and can be performed on the detected Lamb wave signals prior to calculating a symmetry parameter.

To avoid a missing a crack at or near the countersink that is positioned in line with the first location of Lamb wave generation and thus symmetrical with both first and second detection positions, at 260 of the exemplary method, a third Lamb wave is generated at a second position, where the second position is not the same as the first position. Referring to FIGS. 1A and 1B, the Lamb wave generator 110 can be moved to the second location by a technician or Lamb wave generator 210 by robotic positioning arm 230.

At 270, the second Lamb wave propagates towards the rivet and, subsequent to its interaction with the rivet and/or countersink, is detected at a third position. At 280, a fourth Lamb wave is generated at the second location and at 290 the fourth Lamb wave is detected subsequent to its interaction with the rivet and/or countersink. At 299, a second symmetry parameter is calculated based on the third and fourth Lamb waves detected at the third and fourth positions.

Figure 3B:
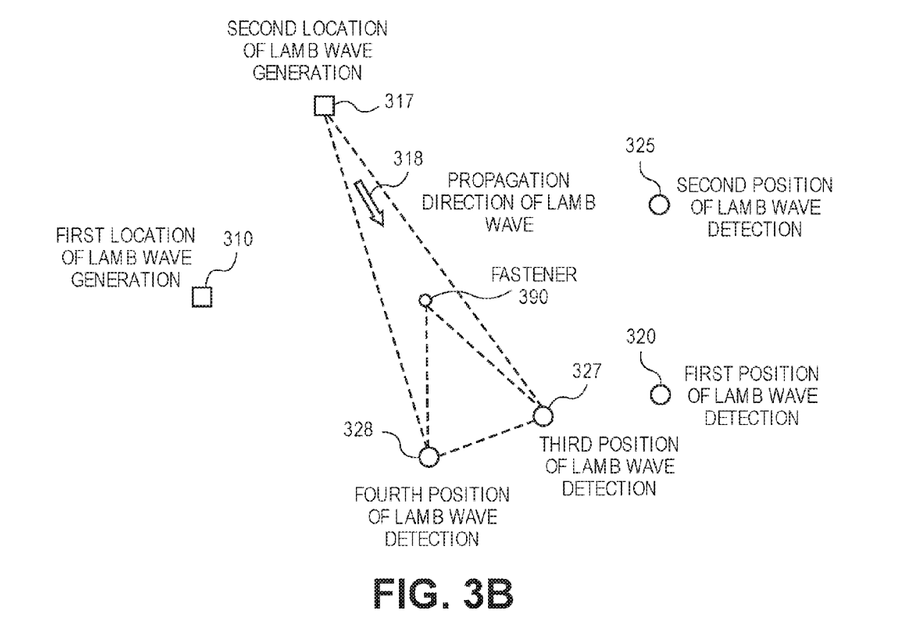

The symmetry of the third and fourth positions is further illustrated in FIG. 3B. A third Lamb wave is generated at a second location 317. The third Lamb wave propagates in a direction represented by arrow 318 towards rivet 390. After the third Lamb wave interacts with rivet and/or countersink 390, it is detected at a third position 327. A fourth Lamb wave is then generated at second location 317 to propagate in the direction represented by arrow 318 towards rivet 390. After the fourth Lamb wave interacts with rivet and/or countersink 390, it is detected at a fourth position 328. As shown by the dotted lines, third position 327 is symmetrical to fourth position 328 with respect to rivet 390 and second location 317. In other words, second location 317, third position 327, and fourth position 328 also form an isosceles triangle. Similarly, location of rivet 390, third position 327, and fourth position 328 also form an isosceles triangle.

Figure 4:
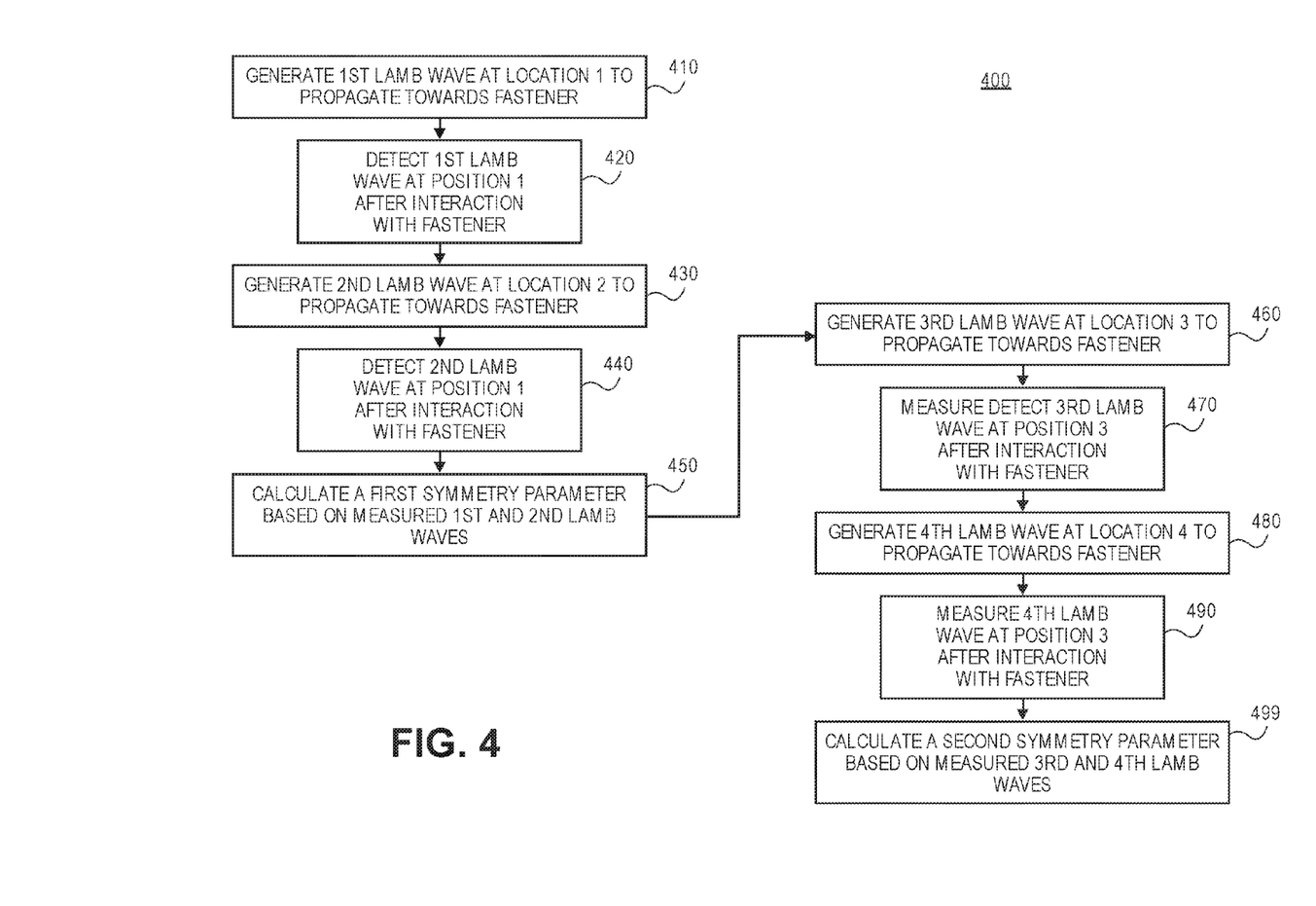
FIG. 4 depicts another method for detecting cracks in thin walled structures using Lamb waves in accordance with an example of the present teachings.

FIG. 4 depicts another exemplary method 400 for non-destructively detecting cracks at the countersink of a fastener. In exemplary method 400, Lamb waves are generated at two symmetrical locations for each Lamb wave detection position. At 410, a first Lamb wave is generated at a first location. For example, referring to FIG. 1, S-EMAT 110 can generate a first Lamb wave in aircraft skin 180 that propagates towards rivet 190.

At 420, subsequent to the first Lamb wave interacting with the countersunk rivet 190, the first Lamb wave is detected at a first position. For example, referring to FIG. 1, Lamb wave detector 120 can detect the first Lamb wave in aircraft skin 180 after it interacts with the rivet/countersink 190.

At 430, a second Lamb wave is generated at a second location on the aircraft skin. The second Lamb wave also propagates towards the rivet. The second location (where the second Lamb wave is generated) is symmetrical to the first location (where the first Lamb wave is generated) with respect to the rivet and the first position (where both the first and second lamb waves are detected)

At 440, subsequent to its interaction with the rivet and/or countersink, the second Lamb wave is detected at the first position.

At 450, a first symmetry parameter is determined based on the first and second detected Lamb waves, as explained above.

To avoid a missing a crack at or near the countersink that is positioned in line with the first position of Lamb wave detection and thus symmetrical with both first and second generation positions, at 460 a third Lamb wave is generated at a third location. At 470, the second Lamb wave propagates towards the rivet and, subsequent to its interaction with the rivet and/or countersink, is detected at a second position, where the second position is not the same as the first position. At 480, a fourth Lamb wave is generated at fourth location and at 490 the fourth Lamb wave is detected subsequent to its interaction with the rivet and/or countersink at the second position. At 499, a second symmetry parameter is calculated based on the third and fourth Lamb waves detected at the second position. This is further illustrated in FIG. 3B.

Figure 5:
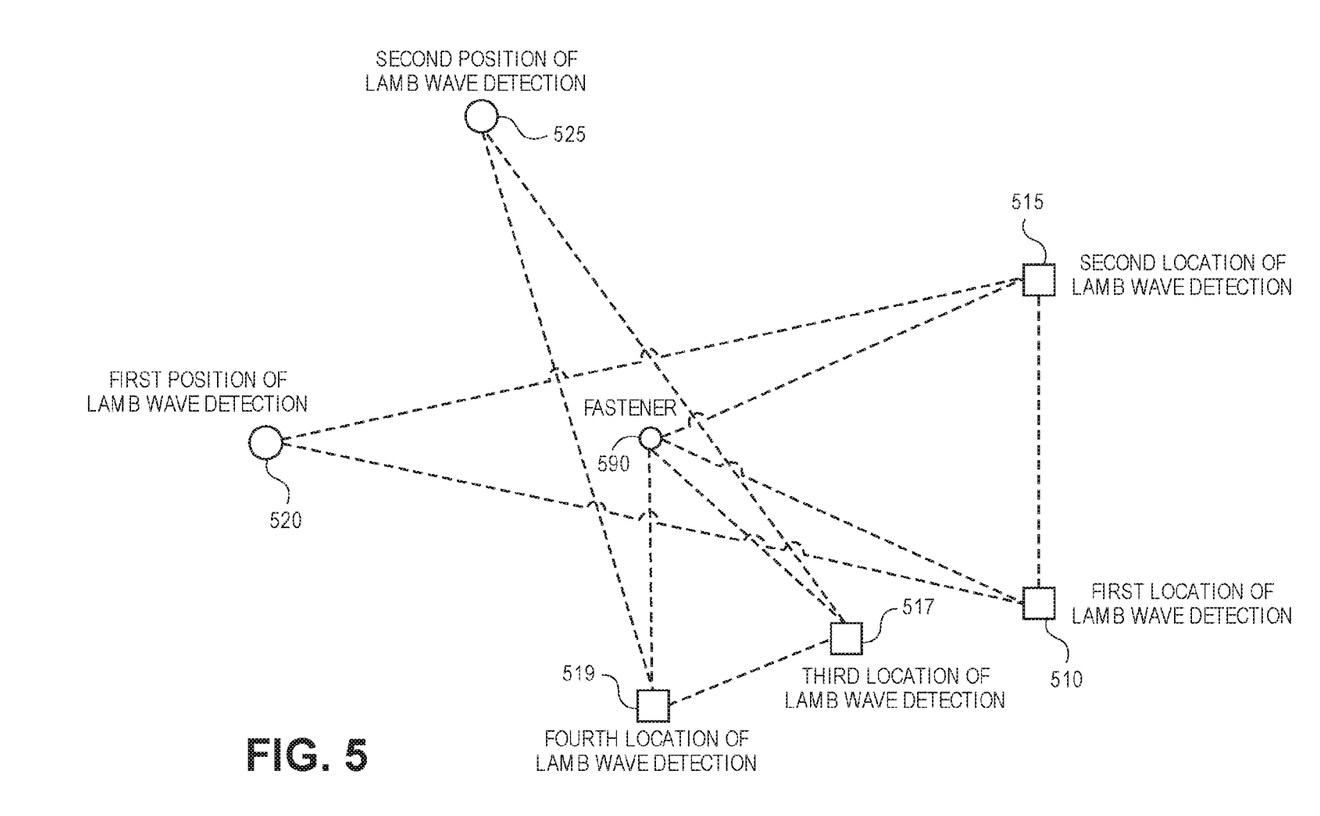
FIG. 5 depicts a symmetry of the detected Lamb waves in accordance with examples of the present teachings.
Figure 6:
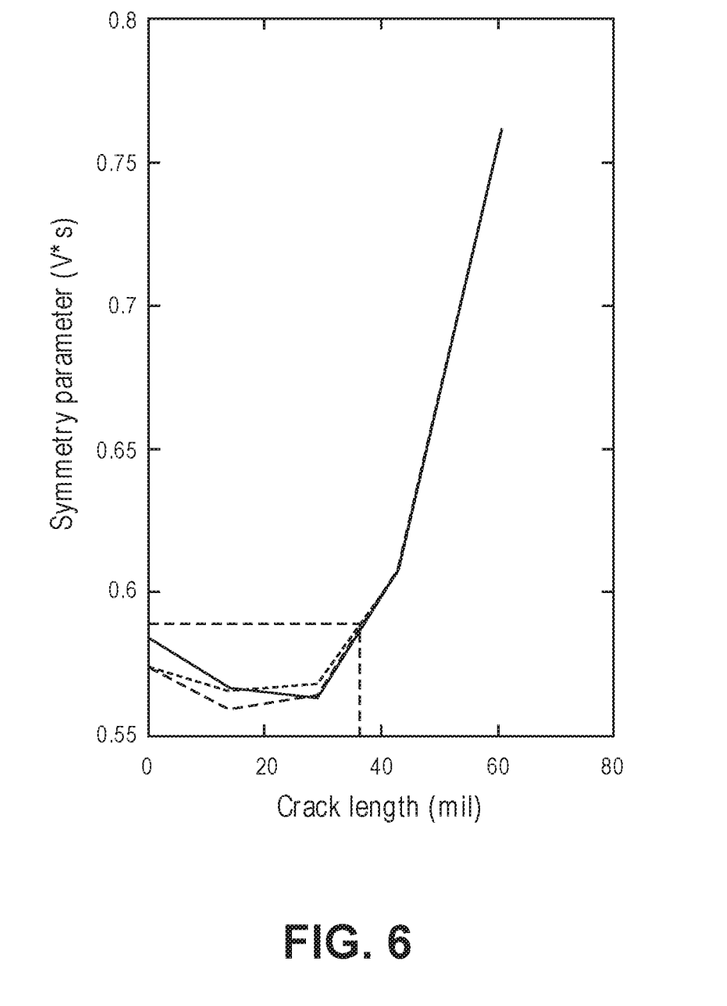
FIG. 6 is a graph showing an example of calculated symmetry parameters in accordance with examples of the present teachings.

The symmetry of the two generation locations for each detection position is further illustrated in FIG. 5, where a first Lamb wave is generated at a first location 510. The first Lamb wave propagates in a direction towards a rivet 590. After the first Lamb wave interacts with rivet and/or countersink 590, it is detected at a first position 520. A second Lamb wave is then generated at a second location 515 to propagate in a direction towards rivet 390. After the second Lamb wave interacts with rivet and/or countersink 390, it is detected at a first position 520. As shown by the dotted lines, first location 510 is symmetrical to second location 515 with respect to rivet 590 and first position 520. In other words, first location 510, second location 515, and first position 520 form an isosceles triangle. Similarly, location of rivet 590, first location 510, and second location 515 also form an isosceles triangle.

FIG. 5 further shows the symmetry of the third and fourth locations. A third Lamb wave is generated at a third location 517. The third Lamb wave propagates in a direction towards rivet 590. After the third Lamb wave interacts with rivet and/or countersink 590, it is detected at a second position 525. A fourth Lamb wave is then generated at a fourth location 519 to propagate in the direction towards rivet 390. After the fourth Lamb wave interacts with rivet and/or countersink 390, it is detected at second position 525. As shown by the dotted lines, third location 517 is symmetrical to fourth location 519 with respect to rivet 390 and second position 525. In other words, third location 517, fourth location 519, and second position 525 also form an isosceles triangle. Similarly, location of rivet 390, third location 517, and fourth location 519 also form an isosceles triangle. One of ordinary skill in the art understands that the disclosed methods contemplate simultaneous generation and/or detection of the Lamb waves.

In another exemplary example, a Lamb can be simultaneously detected at two locations. Referring to FIG. 1C, Lamb wave detector 120 can include two detectors that are spaced apart from each other. The two detectors of Lamb wave detector 120 can detect a first Lamb wave at first position 320 and also detect the first Lamb wave at a second position 325, as shown on FIG. 3A. In other words, the first Lamb wave can be detected at two symmetrical positions at the same time. Similarly, Lamb wave detector 120 can include two detectors to detect the second Lamb wave at third position 327 and fourth position 328 at the same time, as shown in FIG. 3B. One of ordinary skill in the art will understand that detection of Lamb waves at more than two symmetric positions can be accomplished. For example, detection at four or more symmetric positions can be implemented for continuous symmetry measurement.

EXAMPLE

Using an exemplary system and method according to the present teachings, a crack was detected in a countersink of a rivet hole. A rivet hole, approximately ⅛ inches in diameter with a ¼ inch diameter counter sink, was drilled in a 2024 aluminum plate. The aluminum plate was 0.08″ thick. Cracks of 14, 29, 43, and 61 mil were placed in the countersink. Lamb waves were generated by a PZT emitter located about 1 inch from the countersunk rivet hole to propagate towards the countersunk rivet hole. After interacting with the countersunk rivet hole, the Lamb waves were detected by a piezoelectric sensor located about an inch away from the countersunk rivet hole. The Lamb waves were detected by the piezoelectric sensor at two sets of locations symmetric with respect to the Lamb wave generator and rivet hole, in a manner similar to that depicted in FIGS. 3A and 3B. The detected Lamb wave signals were filtered, subject to a Hilbert transformation, and an analytic function calculated to build a signal envelope. Symmetry parameters were then calculated by integrating the envelope a characteristic time from the time of arrival. Three sets of measurements were taken and the results plotted as crack length versus symmetry parameter as depicted in FIG. 7. As evident, cracks of more than about 38 mil were detected when the symmetry parameter changed to about 0.57.

Notwithstanding that the numerical ranges and parameters setting forth the broad scope of the present teachings are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5. In certain cases, the numerical values as stated for the parameter can take on negative values. In this case, the example value of range stated as "less than 10" can assume negative values, e.g. −1, −2, −3, −10, −20, −30, etc.

While the present teachings have been illustrated with respect to one or more implementations, alterations and/or modifications can be made to the illustrated examples without departing from the spirit and scope of the appended claims. For example, it will be appreciated that while the process is described as a series of acts or events, the present teachings are not limited by the ordering of such acts or events. Some acts may occur in different orders and/or concurrently with other acts or events apart from those described herein. Also, not all process stages may be required to implement a methodology in accordance with one or more aspects or examples of the present teachings. It will be appreciated that structural components and/or processing stages can be added or existing structural components and/or processing stages can be removed or modified. Further, one or more of the acts depicted herein may be carried out in one or more separate acts and/or phases. Furthermore, to the extent that the terms "including," "includes," "having," "has," "with," or variants thereof are used in either the detailed description and the claims, such terms are intended to be inclusive in a manner similar to the term "comprising." The term "at least one of" is used to mean one or more of the listed items can be selected. Further, in the discussion and claims herein, the term "on" used with respect to two materials, one "on" the other, means at least some contact between the materials, while "over" means the materials are in proximity, but possibly with one or more additional intervening materials such that contact is possible but not required. Neither "on" nor "over" implies any directionality as used herein. The term "conformal" describes a coating material in which angles of the underlying material are preserved by the conformal material. The term "about" indicates that the value listed may be somewhat altered, as long as the alteration does not result in nonconformance of the process or structure to the illustrated example. Finally, "exemplary" indicates the description is used as an example, rather than implying that it is an ideal. Other examples of the present teachings will be apparent to those skilled in the art from consideration of the specification and practice of the disclosure herein. It is intended that the specification and examples be considered as exemplary only, with a true scope and spirit of the present teachings being indicated by the following claims.

Terms of relative position as used in this application are defined based on a plane parallel to the conventional plane or working surface of a workpiece, regardless of the orientation of the workpiece. The term "horizontal" or "lateral" as used in this application is defined as a plane parallel to the conventional plane or working surface of a workpiece, regardless of the orientation of the workpiece. The term "vertical" refers to a direction perpendicular to the horizontal. Terms such as "on," "side" (as in "sidewall"), "higher," "lower," "over," "top," and "under" are defined with respect to the conventional plane or working surface being on the top surface of the workpiece, regardless of the orientation of the workpiece.

The invention claimed is:
1. A method for detecting cracks in a structure, the method comprising:
generating a first Lamb wave at a first location, wherein the first Lamb wave propagates towards a fastener in the structure;
detecting, via a detector at a first detector position, a first signal corresponding to the first Lamb wave subsequent to the first Lamb wave's interaction with the fastener;
generating a second Lamb wave at the first location;

detecting, at a second detector position, a second signal corresponding to the second Lamb wave subsequent to the second Lamb wave's interaction with the fastener, wherein the second detector position is symmetric to the first detector position relative to the fastener and the first location; and calculating a first symmetry parameter from the first signal and the second signal, wherein the first symmetry parameter comprises a value representing a comparison of an amplitude of the first signal and an amplitude of the second signal.

2. The method of claim 1, further comprising indicating that a crack exists in the structure when the first symmetry parameter exceeds a predetermined threshold.

3. The method of claim 1, wherein calculating the first symmetry parameter comprises performing one or more of direct subtraction with integration, cross correlation, or integration of the first signal and the second signal.

4. The method of claim 3, wherein the first and second signals are processed by one or more of signal envelope calculation and continuous wavelet analysis prior to calculating the first symmetry parameter.

5. The method of claim 1 further comprising:
generating a third Lamb wave at a second location, wherein the third Lamb wave propagates towards the fastener;
detecting, at a third detector position, a third signal corresponding to the third Lamb wave subsequent to the third Lamb wave's interaction with the fastener;
generating a fourth Lamb wave at the second location;
detecting, at a fourth detector position, a fourth signal corresponding to the fourth Lamb wave subsequent to the fourth Lamb wave's interaction with the fastener, wherein the fourth detector position is symmetric to the third detector position relative to the fastener and the second location; and
calculating a second symmetry parameter from the third signal and the fourth signal, wherein the second symmetry parameter comprises a value representing a comparison of an amplitude of the third signal and an amplitude of the fourth signal.

6. The method of claim 5, further comprising indicating that a crack exists in the structure when the second symmetry parameter exceeds a predetermined threshold.

7. The method of claim 1, wherein generating the first Lamb wave at the first location comprises using one or more of an electromagnetic acoustic transducer (EMAT), a superconducting EMAT (SEMAT), and a pulsed laser to generate the first Lamb wave.

8. The method of claim 1, wherein detecting the first signal corresponding to the first Lamb wave comprises using one or more of an interferometer, a SEMAT, a vibrometer, and a capacitive sensor to measure the first signal.

9. The method of claim 1, wherein detecting the first signal corresponding to the first Lamb wave comprises moving the detector to the first detector position using an automated system, the automated system including a camera and a robotic positioning arm.

10. The method of claim 1, wherein the structure comprises an aircraft skin and the fastener comprises a rivet countersunk in the aircraft skin.

11. A method for detecting cracks in a structure, the method comprising:
generating a first Lamb wave at a first location, wherein the first Lamb wave propagates towards a fastener in the structure;

detecting, at a first detector position, a first signal corresponding to the first Lamb wave subsequent to the first Lamb wave's interaction with the fastener;
generating a second Lamb wave at a second location, wherein the second location is symmetric to the first location relative to the fastener and the first detector position;
detecting, at the first detector position, a second signal corresponding to the second Lamb wave subsequent to the second Lamb wave's interaction with the fastener; and
calculating a first symmetry parameter from the first signal and the second signal, wherein the first symmetry parameter comprises a value representing a comparison of an amplitude of the first signal and an amplitude of the second signal.

12. The method of claim 11, further comprising indicating that a crack exists in the structure when the first symmetry parameter exceeds a predetermined threshold.

13. The method of claim 11, wherein calculating the first symmetry parameter comprises performing one or more of direct subtraction with integration, cross correlation, or integration of the first signal and the second signal.

14. The method of claim 13, wherein the first and second signals are processed by one or more of signal envelope calculation and continuous wavelet analysis prior to calculating the first symmetry parameter.

15. The method of claim 11, further comprising:
generating a third Lamb wave at a third location, wherein the third Lamb wave propagates towards the fastener;
detecting, at a second detector position, a third signal corresponding to the third Lamb wave subsequent to the third Lamb wave's interaction with the fastener;
generating a fourth Lamb wave at a fourth location, wherein the fourth location is symmetric to the third location relative to the fastener and the second location;
detecting, at the second detector position, a fourth signal corresponding to the fourth Lamb wave subsequent to the fourth Lamb wave's interaction with the fastener; and
calculating a second symmetry parameter from the third signal and the fourth signal, wherein the second symmetry parameter comprises a value representing a comparison of an amplitude of the third signal and an amplitude of the fourth signal.

16. The method of claim 15, further comprising indicating that a crack exists in the structure when the second symmetry parameter exceeds a predetermined threshold.

17. A system for detecting cracks in a structure comprising:
a Lamb wave generation device that generates a first Lamb wave that propagates towards a fastener in the structure and that generates a second Lamb wave that propagates towards the fastener;
a Lamb wave detection device that provides a first signal corresponding to the first Lamb wave subsequent to the first Lamb wave's interaction with the fastener and provides a second signal corresponding to the second Lamb wave subsequent to the second Lamb wave's interaction with the fastener;
a positioning system that positions the Lamb wave detection device to measure the first signal at a first position and to measure the second signal at second position, wherein the first position is symmetric to the second position relative to the fastener and the Lamb wave generation device; and
a computing system comprising, one or more processors, and
    a memory system comprising one or more non-transitory computer readable media storing instructions that, when executed by the one or more processors, causes the computing system to calculate a symmetry parameter from the first signal and second signal and compare the symmetry parameter to a predetermined threshold,
  wherein the symmetry parameter comprises a value representing a comparison of an amplitude of the first signal and an amplitude of the second signal.

18. The system of claim 17, wherein the positioning system comprises a camera and a robotic positioning arm.

19. The system of claim 17, further comprising a display that shows a representation of the comparison of the symmetry parameter to the predetermined threshold.

20. The system of claim 17, further comprising an indicator to show that a crack has been detected.

21. A method for detecting cracks in a structure, the method comprising:

generating a first Lamb wave at a first location, wherein the first Lamb wave propagates towards a fastener in the structure;

detecting, at a first detector position, a first signal corresponding to the first Lamb wave subsequent to the first Lamb wave's interaction with the fastener;

detecting, at a second detector position, a second signal corresponding to the first Lamb wave subsequent to the first Lamb wave's interaction with the fastener, wherein the second detector position is symmetric to the first detector position relative to the fastener and the first location; and calculating a first symmetry parameter from the first signal and the second signal, wherein the first symmetry parameter comprises a value representing a comparison of an amplitude of the first signal and an amplitude of the second signal.

* * * * *